United States Patent
Yamada et al.

(10) Patent No.: US 6,897,886 B2
(45) Date of Patent: May 24, 2005

(54) INDOLYLPHTHALIDE COMPOUND AND THERMAL RECORDING MATERIAL USING THE SAME

(75) Inventors: Satoru Yamada, Shizuoka-ken (JP); Kazumori Minami, Shizuoka-ken (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 7 days.

(21) Appl. No.: 10/682,797

(22) Filed: Oct. 10, 2003

(65) Prior Publication Data

US 2004/0135871 A1 Jul. 15, 2004

(30) Foreign Application Priority Data

Oct. 16, 2002 (JP) .................. 2002-301783
Nov. 8, 2002 (JP) .................. 2002-324882

(51) Int. Cl.[7] ................................. B41J 2/38
(52) U.S. Cl. .................................. 347/187
(58) Field of Search .................. 347/187, 188, 347/195, 101, 102; 503/200, 226

(56) References Cited

U.S. PATENT DOCUMENTS

| | | |
|---|---|---|
| 4,181,328 A | 1/1980 | Satomura et al. |
| 4,436,920 A | 3/1984 | Sato et al. |
| 4,480,052 A | 10/1984 | Ichijima et al. |
| 4,508,897 A | 4/1985 | Bedekovic et al. |
| 4,587,539 A | 5/1986 | Bedekovic et al. |

(Continued)

FOREIGN PATENT DOCUMENTS

| | | |
|---|---|---|
| GB | 2 140 449 A | 11/1984 |
| JP | 57-179836 A | 11/1982 |
| JP | 60-23992 B2 | 6/1985 |
| JP | 60-123556 A | 7/1985 |
| JP | 60-123557 A | 7/1985 |
| JP | 61-4856 B2 | 2/1986 |
| JP | 61-168664 A | 7/1986 |
| JP | 61-291654 A | 12/1986 |
| JP | 62-270662 A | 11/1987 |

Primary Examiner—K. Feggins
(74) Attorney, Agent, or Firm—Sughrue Mion, PLLC (57) ABSTRACT

A thermal recording material comprising, on a substrate, a thermal recording layer which includes an electron-donating dye precursor and an electron-accepting compound, wherein at least one kind of the electron-donating dye precursor is an indolylphthalide compound represented by general formula (1):

General formula (1)

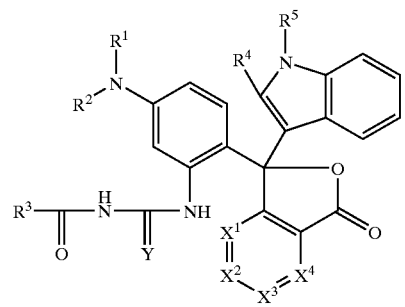

wherein $R^1$ and $R^2$ each independently represent a hydrogen atom, an alkyl group or the like, provided that $R^1$ and $R^2$ do not represent a hydrogen atom at the same time, and $R^1$ and $R^2$ may form a bond therebetween to collectively represent a single cycloamino structure; $R^3$ represents an alkyl group or the like; $R^4$ and $R^5$ each independently represent a hydrogen atom, an alkyl group or an aryl group; $X^1$, $X^2$, $X^3$ and $X^4$ each independently represent N or CH; and Y represents an oxygen atom or a sulfur atom.

18 Claims, 1 Drawing Sheet

U.S. PATENT DOCUMENTS

| | | |
|---|---|---|
| 4,660,060 A | 4/1987 | Hung et al. |
| 4,668,790 A | 5/1987 | Bedekovic et al. |
| 4,675,407 A | 6/1987 | Bedekovic et al. |
| 4,695,636 A | 9/1987 | Bedekovic et al. |
| 4,996,537 A * | 2/1991 | Kishimi ........................ 347/188 |
| 5,260,715 A * | 11/1993 | Kishimi ........................ 347/195 |
| 6,395,679 B1 * | 5/2002 | Takeuchi ..................... 503/200 |
| 6,667,275 B2 * | 12/2003 | Sano et al. ................... 503/200 |

* cited by examiner

FIG.1

INDOLYLPHTHALIDE COMPOUND AND THERMAL RECORDING MATERIAL USING THE SAME

CROSS-REFERENCE TO RELATED APPLICATION

This application claims priority under 35 USC 119 from Japanese Patent Application Nos. 2002-301783 and 2002-324882, the disclosures of which are incorporated by reference herein.

BACKGROUND OF THE INVENTION

1. Field of the Invention

The present invention relates to an indolylphthalide compound and a thermal recording material using the same.

2. Description of the Related Art

Recording materials using an electron-donating dye precursor and an electron-accepting compound have been well known as pressure-sensitive papers, heat-sensitive papers, photosensitive/pressure-sensitive papers, conductive thermal recording papers, thermal transfer papers or the like. Detailed information on the recording materials is disclosed, for example, in U.K. Patent No. 2,140,449, U.S. Pat. Nos. 4,480,052 and 4,436,920, Japanese Patent Application Publication (JP-B) No. 60-23992, Japanese Patent Application Laid-Open (JP-A) Nos. 57-179836, 60-123556 and 60-123557, and the like.

In recent years, serious studies have been conducted on improvements to a recording material with respect to image density, color fastness of an image portion, light fastness of a white portion, and the like. Various examples of known electron-donating dye precursors that form images in colors ranging from blue to cyan include triphenylmethanephthalide-based compounds, phenothiazine-based compounds, indolylphthalide-based compounds and the like.

Among indolylphthalide-based compounds, some examples of a so-called indolyl(aza)phthalide-based compound have been known that are obtained by substituting a nitrogen atom for a carbon atom on a benzene ring in the phthalide moiety. Concrete examples thereof are detailed in JP-B No. 61-4856, JP-A Nos. 61-168664, 61-291654 and 62-270662, and the like.

Although the compounds described above form images in colors ranging from blue to cyan with good density, they have problems in that they satisfy neither of performances of good color fastness of an image upon exposure to light and high color development performance. Furthermore, a conventional indolylphthalide compound has an absorption band having a gradual slope on the short wavelength side of the first absorption band. The gradual slope causes a developed color image to have a low chroma.

SUMMARY OF THE INVENTION

A first aspect of the present invention is to provide an indolylphthalide compound that forms an image in a color in the range of blue to cyan with a good chroma.

A second aspect of the invention is to provide a thermal recording material using the indolylphthalide compound.

The above objects are achieved with the following means.
(1) An indolylphthalide compound represented by the general formula (1):

General formula (1)

wherein $R^1$ and $R^2$ each independently represent a hydrogen atom, an alkyl group, a cycloalkyl group, an aralkyl group or an aryl group, provided that $R^1$ and $R^2$ do not represent a hydrogen atom at the same time, and $R^1$ and $R^2$ may form a bond therebetween to collectively represent a single cycloamino structure; $R^3$ represents an alkyl group, a cycloalkyl group, an aralkyl group, an aryl group or an alkoxy group; $R^4$ and $R^5$ each independently represent a hydrogen atom, an alkyl group or an aryl group; $X^1$, $X^2$, $X^3$ and $X^4$ each independently represent N or CH; and Y represents an oxygen atom or a sulfur atom.

(2) A thermal recording material comprising, on a substrate, a thermal recording layer which includes an electron-donating dye precursor and an electron-accepting compound, wherein at least one kind of the electron-donating dye precursor is represented by the general formula (1):

General formula (1)

wherein $R^1$ and $R^2$ each independently represent a hydrogen atom, an alkyl group, a cycloalkyl group, an aralkyl group or an aryl group, provided that $R^1$ and $R^2$ do not represent a hydrogen atom at the same time, and $R^1$ and $R^2$ may form a bond therebetween to collectively represent a single cycloamino structure; $R^3$ represents an alkyl group, a cycloalkyl group, an aralkyl group, an aryl group or an alkoxy group; $R^4$ and $R^5$ each independently represent a hydrogen atom, an alkyl group or an aryl group; $X^1$, $X^2$, $X^3$ and $X^4$ each independently represent N or CH; and Y represents an oxygen atom or a sulfur atom.

DETAILED DESCRIPTION OF THE INVENTION

Indolylphthalid Compound

An indolylphthalide compound of the present invention is represented by a general formula (1). By employing an indolylphthalide compound of the present invention as an electron-donating dye precursor of a thermal recording material, an image with a good chroma can be obtained in a color in the range of blue to cyan.

General formula (1)

In the general formula (1), $R^1$ and $R^2$ each independently represent a hydrogen atom, an alkyl group, a cycloalkyl group, an aralkyl group or an aryl group, provided that $R^1$ and $R^2$ do not represent a hydrogen atom at the same time, and $R^1$ and $R^2$ may form a bond therebetween to collectively represent a single cycloamino structure; $R^3$ represents an alkyl group, a cycloalkyl group, an aralkyl group, an aryl group or an alkoxy group; $R^4$ and $R^5$ each independently represent a hydrogen atom, an alkyl group or an aryl group; $X^1$, $X^2$, $X^3$ and $X^4$ each independently represent N or CH; and Y represents an oxygen atom or a sulfur atom.

In the general formula (1) described above, preferable examples of $R^1$ and $R^2$ include an alkyl group having 1 to 18 carbon atoms, a cycloalkyl group having 4 to 12 carbon atoms, an aralkyl group having 7 to 18 carbon atoms or an aryl group having 6 to 12 carbon atoms. Each of the groups may also further have a substituent selected from the group consisting of an alkyl group having 1 to 8 carbon atoms, an alkoxy group having 1 to B carbon atoms, an aryl group having 6 to 10 carbon atoms, an aryloxy group having 6 to 10 carbon atoms and a halogen atom.

Preferable concrete examples of $R^1$ and $R^2$ include a methyl group, an ethyl group, an n-propyl group, an i-propyl group, an n-butyl group, an i-butyl group, a sec-butyl group, an n-pentyl group, an i-pentyl group, an n-hexyl group, an n-octyl group, a 2-ethylhexyl group, an n-decyl group, an n-dodecyl group, a cyclopentyl group, a cyclohexyl group, a benzyl group, a 2-phenethyl group, a 1-phenethyl group, a phenyl group, a p-tolyl group, a p-methoxyphenyl group, a p-chlorophenyl group, 2-methoxyethyl group, a 2-(2-methoxyethoxy)ethyl group, a 2-phenoxyethyl group, a 2-phenoxypropyl group, a 3-phenoxypropyl group and the like, of which an particularly preferable example is an n-propyl group.

$R^1$ and $R^2$ may form a bond therebetween to collectively represent a single cycloamino structure and preferable concrete examples of the cycloamino structure include a 1-pyrrolidyl group, a piperidino group, a morpholino group and the like, of which an 1-pyrrolidyl group is particularly preferable.

In the general formula (1), in the case where $R^3$ represents an alkyl group, a cycloalkyl group, an aralkyl group or an aryl group, preferable examples of $R^3$ include an alkyl group having 1 to 18 carbon atoms, a cycloalkyl group having 5 or 6 carbon atoms, an aralkyl group having 7 to 18 carbon atoms or an aryl group having 6 to 12 carbon atoms, of which particularly preferable examples are an alkyl group having 1 to 12 carbon atoms, a cycloalkyl group having 6 carbon atoms, an aralkyl group having 7 to 12 carbon atoms and an aryl group having 6 to 10 carbon atoms. Each of the groups may also further have, as a substituent, an alkoxy group, a halogen atom or the like.

Preferable concrete examples of $R^3$ in the case where $R^3$ represents an alkyl group, a cycloalkyl group, an aralkyl group or an aryl group include a methyl group, an ethyl group, an n-propyl group, an i-propyl group, an n-butyl group, an i-butyl group, a sec-butyl group, an n-pentyl group, an i-pentyl group, an n-hexyl group, an n-octyl group, a 2-ethylhexyl group, an n-decyl group, an n-dodecyl group, a cyclopentyl group, a cyclohexyl group, a benzyl group, a 2-phenethyl group, a 1-phenethyl group, a phenyl group, a p-tolyl group, a chloromethyl group, a dichloromethyl group, a trichloromethyl group and the like, of which an particularly preferable example is a phenyl group.

In the case where $R^3$ represents an alkoxy group, if $R^3$ is otherwise represented as $OR^{31}$, $R^{31}$ is preferably exemplified as follows: an alkyl group having 1 to 18 carbon atoms, a cycloalkyl group having 5 or 6 carbon atoms, an aralkyl group having 7 to 18 carbon atoms or an aryl group having 6 to 12 carbon atoms, of which particularly preferable examples are an alkyl group having 1 to 12 carbon atoms, a cycloalkyl group having 6 carbon atoms, an aralkyl group having 7 to 12 carbon atoms or an aryl group having 6 to 10 carbon atoms. Each of the groups may also further have an alkoxy group, a halogen atom or the like as a substituent.

Preferable examples of $R^3$ in the case where $R^3$ represents an alkoxy group include a methoxy group, an ethoxy group, an n-propoxy group, an i-propoxy group, an n-butoxy group, an i-butoxy group, a sec-butoxy group, an n-pentyloxy group, an i-pentyloxy group, an n-hexyloxy group, an n-octyloxy group, a 2-ethylhexyloxy group, an n-decyloxy group, an n-dodecyloxy group, a cyclopentyloxy group, a cyclohexyloxy group, a benzyloxy group, a 2-phenethyloxy group, 1-phenethyloxy group, a phenoxy group, a p-tolyloxy group, a chloromethoxy group, a dichloromethoxy group, a trichloromethoxy group and the like, of which an particularly preferable example is an ethoxy group.

In the general formula (1) described above, preferable examples of $R^4$ include a hydrogen atom, an alkyl group having 1 to 4 carbon atoms or an aryl group having 6 to 10 carbon atoms and more preferably a hydrogen atom, a methyl group or a phenyl group, of which an particularly preferable example is a methyl group. Note that the phenyl group may also have a substituent.

In the general formula (1) described above, preferable examples of $R^5$ include a hydrogen atom, an alkyl group having 1 to 18 carbon atoms or an aryl group having 6 to 15 carbon atoms and more preferably an alkyl group having 1 to 12 carbon atoms, an aryl group having 6 to 10 carbon atoms, of which an particularly preferable example is an ethyl group.

Each of the groups described above may also further have, as a substituent, an alkyl group having 1 to 8 carbon atoms, an alkoxy group having 1 to 8 carbon atoms, an aryl group having 6 to 10 carbon atoms, an aryloxy group having 6 to 10 carbon atoms, a halogen atom or the like.

In the general formula (1) described above, in the case where any one of $X^1$, $X^2$, $X^3$ and $X^4$ represents N, $X^1$ preferably represents N and in the case where any two of $X^1$, $X^2$, $X^3$ and $X^4$ represent N, $X^1$ and $X^4$ preferably represent N.

In the general formula (1) described above, Y represents an oxygen atom or a sulfur atom, of which a particularly preferable example is an oxygen atom.

An indolylphthalide compound of the present invention is preferably represented by the following general formula (2).

General formula (2)

The general formula (2) corresponds to the general formula (1) except in that, in the general formula (2), $X^2$, $X^3$ and $X^4$ each represent CH, and Y represents an oxygen atom.

In the general formula (2), $R^1$ and $R^2$ each independently represent a hydrogen atom, an alkyl group, a cycloalkyl group, an aralkyl group or an aryl group, provided that $R^1$ and $R^2$ do not represent a hydrogen atom at the same time, and $R^1$ and $R^2$ may form a bond therebetween to collectively represent a single cycloamino structure; $R^3$ represents an alkyl group, a cycloalkyl group, an aralkyl group, an aryl group or an alkoxy group; $R^4$ and $R^5$ each independently represent a hydrogen atom, an alkyl group or an aryl group; and $X^1$ represents N or CH.

In the general formula (2), concrete examples of $R^1$ to $R^5$ include an atom and groups similar to the atom and the groups of the general formula (1).

Concrete examples of indolylphthalide compounds of the present invention represented by the general formulae (1) and (2) are presented below, while the invention is not limited to the following concrete examples.

TABLE 1

| Compound | $R^3$ | $R^5$ |
|---|---|---|
| 1 | $CH_3$ | Et |
| 2 | Et | Et |
| 3 | $^nBu$ | Et |
| 4 | $CH_2Ph$ | Et |
| 5 | Ph | Et |
| 6 | $(C_6H_4)CH_3$ | Et |
| 7 | $OCH_3$ | Et |
| 8 | OEt | Et |
| 9 | $O^nBu$ | Et |
| 10 | $OCH_2Ph$ | Et |
| 11 | OPh | Et |
| 12 | $O(C_6H_4)CH_3$ | Et |

TABLE 1-continued

| Compound | $R^3$ | $R^5$ |
|---|---|---|
| 13 | $CH_3$ | $C_8H_{17}$ |
| 14 | Et | $C_8H_{17}$ |
| 15 | $^nBu$ | $C_8H_{17}$ |
| 16 | $CH_2Ph$ | $C_8H_{17}$ |
| 17 | Ph | $C_8H_{17}$ |
| 18 | $(C_6H_4)CH_3$ | $C_8H_{17}$ |
| 19 | $OCH_3$ | $C_8H_{17}$ |
| 20 | OEt | $C_8H_{17}$ |
| 21 | $O^nBu$ | $C_8H_{17}$ |
| 22 | $OCH_2Ph$ | $C_8H_{17}$ |
| 23 | OPh | $C_8H_{17}$ |
| 24 | $O(C_6H_4)CH_3$ | $C_8H_{17}$ |

TABLE 2

| Compound | $R^3$ | $R^5$ |
|---|---|---|
| 25 | $CH_3$ | Et |
| 26 | Et | Et |
| 27 | $^nBu$ | Et |
| 28 | $CH_2Ph$ | Et |
| 29 | Ph | Et |
| 30 | $(C_6H_4)CH_3$ | Et |
| 31 | $OCH_3$ | Et |
| 32 | OEt | Et |
| 33 | $O^nBu$ | Et |
| 34 | $OCH_2Ph$ | Et |
| 35 | OPh | Et |
| 36 | $O(C_6H_4)CH_3$ | Et |
| 37 | $CH_3$ | $C_8H_{17}$ |
| 38 | Et | $C_8H_{17}$ |
| 39 | $^nBu$ | $C_8H_{17}$ |
| 40 | $CH_2Ph$ | $C_8H_{17}$ |
| 41 | Ph | $C_8H_{17}$ |
| 42 | $(C_6H_4)CH_3$ | $C_8H_{17}$ |
| 43 | $OCH_3$ | $C_8H_{17}$ |
| 44 | OEt | $C_8H_{17}$ |
| 45 | $O^nBu$ | $C_8H_{17}$ |
| 46 | $OCH_2Ph$ | $C_8H_{17}$ |
| 47 | OPh | $C_8H_{17}$ |
| 48 | $O(C_6H_4)CH_3$ | $C_8H_{17}$ |

TABLE 3

| Compound | R³ | R⁵ |
| --- | --- | --- |
| 49 | CH₃ | Et |
| 50 | Ph | Et |
| 51 | OCH₃ | Et |
| 52 | OPh | Et |
| 53 | CH₃ | C₈H₁₇ |
| 54 | Ph | C₈H₁₇ |
| 55 | OCH₃ | C₈H₁₇ |
| 56 | OPh | C₈H₁₇ |

TABLE 4

| Compound | R³ | R⁵ |
| --- | --- | --- |
| 57 | CH₃ | Et |
| 58 | Ph | Et |
| 59 | OCH₃ | Et |
| 60 | OPh | Et |
| 61 | CH₃ | C₈H₁₇ |
| 62 | Ph | C₈H₁₇ |
| 63 | OCH₃ | C₈H₁₇ |
| 64 | OPh | C₈H₁₇ |

TABLE 5

| Compound | R³ | R⁵ |
| --- | --- | --- |
| 65 | CH₃ | Et |
| 66 | Ph | Et |

TABLE 5-continued

| Compound | R³ | R⁵ |
| --- | --- | --- |
| 67 | OCH₃ | Et |
| 68 | OPh | Et |
| 69 | CH₃ | C₈H₁₇ |
| 70 | Ph | C₈H₁₇ |
| 71 | OCH₃ | C₈H₁₇ |
| 72 | OPh | C₈H₁₇ |

TABLE 6

| Compound | R³ | R⁵ |
| --- | --- | --- |
| 73 | Ph | Et |
| 74 | OPh | Et |

TABLE 7

| Compound | R³ | R⁵ |
| --- | --- | --- |
| 75 | Ph | Et |
| 76 | OPh | Et |

TABLE 8

| Compound | R³ | R⁵ |
|---|---|---|
| 77 | Ph | Et |
| 78 | OPh | Et |

TABLE 9

| Compound | R³ | R⁵ |
|---|---|---|
| 79 | Ph | Et |
| 80 | OPh | Et |

A synthesizing method for the indolylphthalide compound of the present invention is described in JP-A No. 8-337727.

Thermal Recording Material

A thermal recording material of the present invention is a thermal recording material comprising, on a substrate, a thermal recording layer which includes an electron-donating dye precursor and an electron-accepting compound, wherein at least one kind of the electron-donating dye precursor is an indolylphthalide compound represented by the general formula (1).

The electron-donating dye precursor is preferably an indolylphthalide compound represented by the general formula (2).

In the present invention, the indolylphthalide compound represented by the general formula (1), which is used as the electron-donating dye precursor, can be used together with various kinds of conventionally known compounds described below, such as a triphenylmethanephthalide-based compound, a fluoran-based compound, a phenothiazine-based compound, an indolylphthalide-based compound, a leucoauramine-based compound, a rhodaminelactam-based compound, a triphenylmethane-based compound, a triazene-based compound, a spiropyran-based compound, a fluorene-based compound and the like.

Concrete examples of phthalides are disclosed in U.S. Reissued Patent No. 23,024 and U.S. Pat. Nos. 3,491,111, 3,491,112, 3,491,116, and 3,509,174. Concrete examples of fluorans are disclosed in U.S. Pat. Nos. 3,624,107, 3,627, 787, 3,641,011, 3,462,828, 3,681,390, 3,920,510 and 3,959, 571. Concrete examples of spirodipyrans are disclosed in U.S. Pat. No. 3,971,808. Concrete examples of pyridine-based compounds and pyrazine-based compounds are disclosed in U.S. Pat. Nos. 3,775,424, 3,853,869 and 4,246, 318. Concrete examples of a fluorene-based compound are disclosed in JP-A No. 63-94878 and the like.

In the present invention, while a coating amount of the electron-donating dye precursor is not specifically defined, the coating amount is preferably in the range of 0.1 to 2.0 g/m², and particularly preferably in the range of 0.2 to 1.5 g/m².

If the coating amount is less than 0.1 g/m², a color density may decrease, and on the other hand, if the coating amount exceeds 2.0 g/m², light fastness may decrease.

In the case where a known electron-donating dye precursor is employed together with the electron-donating dye precursor of the present invention, a proportion of the electron-donating dye precursor of the present invention relative to a total amount of the electron-donating dye precursors is preferably 30% by mass or more, and particularly preferably 60% by mass or more.

Examples of the electron-accepting compound employed in the thermal recording material of the present invention include a phenol derivative, a salicylic acid derivative, an aromatic carboxylic acid metal salt, acid clay, bentonite, a novolak resin, a metal treated novolak resin, a metal complex and the like.

Concrete examples thereof are disclosed in JP-B Nos. 40-9309 and 45-14039, JP-A Nos. 52-140483, 48-51510, 57-210886, 58-87089, 58-11286, 60-176795 and 61-95988, and the like.

The electron-accepting compound employed in the thermal recording material of the present invention is contained as an electron-accepting compound (a color-developing agent) which reacts with an electron-donating dye precursor to develop a color.

At least one kind of the electron-accepting compound employed in the thermal recording material of the present invention is preferably a salicylic acid derivative metal salt represented by the following general formula (3):

General formula (3)

wherein, in the general formula (3), $Z^1$, $Z^2$, $Z^3$ and $Z^4$ each independently represent a hydrogen atom, an alkyl group, a cycloalkyl group, an aralkyl group, an aryl group, a hydroxyl group or a halogen atom; n represents 2 or 3; and M represents Al, Zn or Cu.

In the general formula (3), an alkyl group represented by $Z^1$, $Z^2$, $Z^3$ or $Z^4$ is preferably an alkyl group having 1 to 18 carbon atoms. The alkyl group may also further have, as a substituent, an alkyl group having 1 to 8 carbon atoms, an aryl group having 6 to 10 carbon atoms, or the like.

A cycloalkyl group represented by $Z^1$, $Z^2$, $Z^3$ or $Z^4$ is preferably a cycloalkyl group having 5 or 6 carbon atoms. The cycloalkyl group may also further have, as a substituent, an alkyl group having 1 to 8 carbon atoms, an aryl group having 6 to 10 carbon atoms, or the like.

An aralkyl group represented by $Z^1$, $Z^2$, $Z^3$ or $Z^4$ is preferably an aralkyl group having 7 to 18 carbon atoms, and more preferably an aralkyl group having 7 to 12 carbon atoms. The aralkyl group may also further have, as a substituent, an alkyl group having 1 to 8 carbon atoms, an alkoxy group having 1 to 8 carbon atoms, an aryl group having 6 to 10 carbon atoms, an aryloxy group having 6 to 10 carbon atoms, a halogen atom, or the like.

An aryl group represented by $Z^1$, $Z^2$, $Z^3$ or $Z^4$ is preferably an aryl group having 6 to 10 carbon atoms. The aryl group may also further have, as a substituent, an alkyl group having 1 to 8 carbon atoms, an aryl group having 6 to 10 carbon atoms, or the like.

Preferable concrete examples of an alkyl group, a cycloalkyl group, an aralkyl group or an aryl group represented by $Z^1$, $Z^2$, $Z^3$ or $Z^4$ include an ethyl group, an n-propyl group, an i-propyl group, an n-butyl group, an i-butyl group, a sec-butyl group, an n-pentyl group, an i-pentyl group, an n-hexyl group, an n-octyl group, a 2-ethylhexyl group, an n-decyl group, an n-dodecyl group, a cyclopentyl group, a cyclohexyl group, a benzyl group, a 2-phenethyl group, a 1-phenethyl group, a phenyl group, a p-tolyl group, a p-methoxyphenyl group, a p-chlorophenyl group, a 2-methoxyethyl group, a 2-(2-methoxyethoxy)ethyl group, a 2-phenoxyethyl group, a 2-phenoxypropyl group, a 3-phenoxypropyl group, and the like, among which a particularly preferable example is a 1-phenethy group.

In the general formula (3), n represents 2 or 3, of which 2 is preferable.

In the general formula (3), M represents Al, Zn or Cu, of which Zn is preferable.

Concrete examples of the compound represented by the general formula (3) are shown below. The present invention is, however, not limited to the following examples.

81

82

83

84

85

86

87

88

89

90

91

92

93

94

95

At least one kind of the electron-accepting compound employed in the thermal recording material of the present invention is also preferably a phenol derivative represented by the following general formula (4).

General formula (4)

In the general formula (4), $A^1$ and $A^2$ each independently represent an alkyl group, a cycloalkyl group, an aralkyl group, an aryl group, a hydroxyl group or a halogen atom; n and m each independently represent a number from 0 to 4, and, in the case where n and m both are 2 or more, $A^1$ and $A^2$ may be the same as or different from each other; and L represents a single bond or a divalent linkage group.

An alkyl group represented by $A^1$ or $A^2$ is preferably an alkyl group having 1 to 18 carbon atoms. The alkyl group may also further have, as a substituent, an alkyl group having 1 to 8 carbon atoms, an aryl group having 6 to 10 carbon atoms, or the like.

A cycloalkyl group represented by $A^1$ or $A^2$ is preferably a cycloalkyl group having 5 or 6 carbon atoms. The cycloalkyl group may also further have, as a substituent, an alkyl group having 1 to 8 carbon atoms, an aryl group having 6 to 10 carbon atoms, or the like.

An aralkyl group represented by $A^1$ or $A^2$ is preferably an aralkyl group having 7 to 18 carbon atoms, and more preferably an aralkyl group having 7 to 12 carbon atoms. The aralkyl group may also further have, as a substituent, an alkyl group having 1 to 8 carbon atoms, an alkoxy group having 1 to 8 carbon atoms, an aryl group having 6 to 10 carbon atoms, an aryloxy group having 6 to 10 carbon atoms, a halogen atom, or the like.

An aryl group represented by $A^1$ or $A^2$ is preferably an aryl group having 6 to 10 carbon atoms. The aryl group may also further have, as a substituent, an alkyl group having 1 to 8 carbon atoms, an aryl group having 6 to 10 carbon atoms, or the like.

Preferable concrete examples of an alkyl group, a cycloalkyl group, an aralkyl group or an aryl group represented by $A^1$ or $A^2$ include an ethyl group, an n-propyl group, an i-propyl group, an n-butyl group, an i-butyl group, a sec-butyl group, an n-pentyl group, an i-pentyl group, an n-hexyl group, an n-octyl group, a 2-ethylhexyl group, an n-decyl group, an n-dodecyl group, a cyclopentyl group, a cyclohexyl group, a benzyl group, a 2-phenethyl group, a 1-phenethyl group, a phenyl group, a p-tolyl group, a p-methoxyphenyl group, a p-chlorophenyl group, a 2-methoxyethyl group, a 2-(2-methoxyethoxy)ethyl group, a 2-phenoxyethyl group, a 2-phenoxypropyl group, a 3-phenoxypropyl group, and the like.

L in the general formula (4) represents a single bond or a divalent linkage group, and examples of the divalent linkage group include an alkylene group, an aralkylene group, an arylene group, and the like.

An alkylene group represented by L in the general formula (4) is preferably an alkylene group having 1 to 18 carbon atoms. The alkylene group may also further have, as a substituent, an alkyl group having 1 to 8 carbon atoms, an aryl group having 6 to 10 carbon atoms, or the like.

An aralkylene group represented by L is preferably an aralkylene group having 7 to 12 carbon atoms. The aralkylene group may also further have, as a substituent, an alkyl group having 1 to 8 carbon atoms, an aryl group having 6 to 10 carbon atoms, or the like.

An arylene group represented by L is preferably an arylene group having 6 to 10 carbon atoms. The arylene group may also further have, as a substituent, an alkyl group having 1 to 8 carbon atoms, an aryl group having 6 to 10 carbon atoms, or the like.

Concrete examples of the compound represented by the general formula (4) are shown below. The present invention is, however, not limited to the following examples.

A content of the electron-accepting compound represented by the general formula (3) or (4) in the thermal recording layer is preferably in the range of 0.1 to 50 times, and more preferably in the range of 5 to 30 times, a total amount of the electron-donating dye precursors. If the content is less than 0.1 times, sufficient light fastness is not obtained, and there are chances of color fading of a color developed image, light coloration in a background portion and reduction in color density. On the other hand, if the content exceeds 50 times, there is a chance of great reduction in light fastness.

In the thermal recording layer, a known electron-accepting compound may be properly selected and used together with the electron-donating compound represented by the general formula (3) or (4) in a range in which the known compound does not harm the effects of the present invention.

In the thermal recording material of the present invention, an ultraviolet ray absorber, a fluorescent brightener and an antioxidant, which are known, may be additionally used together with the electron-donating dye precursor and the electron-accepting compound, which are described above, in a range in which the known agent does not harm the effects of the present invention.

Preferable examples of ultraviolet ray absorbers that can be additionally used include a benzophenone-based ultraviolet ray absorber, a benzotriazole-based ultraviolet ray absorber, a salicylic acid-based ultraviolet ray absorber, a cyanoacrylate-based ultraviolet ray absorber, an oxalic acid anilide-based ultraviolet ray absorber, and the like. Concrete examples thereof are disclosed in JP-A Nos. 47-10537, 58-111942, 58-212844, 59-19945, 59-46646, 59-109055 and 63-53544, JP-B Nos. 36-10466, 42-26187, 48-30492, 48-31255, 48-41572, 48-54965 and 50-10726, and U.S. Pat. Nos. 2,719,086; 3,707,375; 3,754,919; and 4,220,711; and the like.

Preferable examples of fluorescent brighteners that can be additionally used include a cumarin-based fluorescent brightener and the like. Concrete examples thereof are disclosed in JP-B Nos. 45-4699, 54-5324, and the like.

Preferable examples of antioxidants that can be additionally used include a hindered amine-based antioxidant, a hindered phenol-based antioxidant, an aniline-based antioxidant, a quinoline-based antioxidant, and the like. Concrete examples thereof are disclosed in JP-A Nos. 59-155090, 60-107383, 60-107384, 61-137770, 61-139481, 61-160287, and the like.

An amount of an ultraviolet ray absorber, a fluorescent brightener or an antioxidant that can be used is preferably in the range of 0.05 to 1.0 g/m$^2$, and particularly preferably in the range of 0.1 to 0.4 g/m$^2$.

In the case where the thermal recording material of the present invention is used in a pressure-sensitive paper, the material may take various modes of usage, which are disclosed in the following earlier granted patents: U.S. Pat. Nos. 2,505,470, 2,505,471, 2,505,489, 2,548,366, 2,712,507, 2,730,456, 2,730,457, 3,103,404, 3,418,250, 4,010,038, and the like. The most general mode of usage is at least a pair of sheets containing an electron-donating dye precursor and an electron-accepting compound, respectively.

A known binder may be added into the thermal recording layer of the thermal recording material of the present invention. Examples thereof include water-soluble polymers such as polyvinyl alcohol and gelatin, and a polymer latex.

In the present invention, examples of modes of usage of the electron-donating dye precursor represented by the general formula (1), the electron-accepting compound represented by the general formula (3) or (4), other electron-donating dye precursors and electron-accepting compounds that are known, and other components include (1) a method in which each of the precursors, compounds and components is dispersed and the dispersion is put into use, (2) a method in which each of the precursors, compounds and components is emulsified and the emulsion is put into use, (3) a method in which each of the precursors, compounds and components is polymer dispersed and the dispersion is put into use, (4) a method in which each of the precursors, compounds and components is latex dispersed and the dispersion is put into use, (5) a method in which each of the precursors, compounds and components is encapsulated in microcapsules (heat-responsive microcapsules) and a dispersion of the microcapsules is put into use, and the like.

To be more concrete, for example, each of an electron-donating dye precursor represented by the general formula (1) and an electron-accepting compound represented by the general formula (3) or (4) (and other components if necessary) together with, for example, a surfactant, a water-soluble polymer and the like may be dispersed with a ball mill, a sand mill or the like and the dispersion is put into use, or alternatively particularly at least one of color developing components (preferably an electron-donating dye precursor) may be encapsulated in microcapsules and then put into use from the viewpoint of preservability.

A preferable mode of usage of the electron-donating dye precursor and the electron-accepting compound is a mode of usage in which at least one of the electron-donating dye precursor and the electron-accepting compound is dispersed and put into use, or in which the electron-donating dye precursor is encapsulated in microcapsules and put into use.

An particularly preferable mode of usage of an electron-donating dye precursor represented by the general formula (1) and an electron-accepting compound represented by the general formula (3) or (4) is a mode of usage in which at least one of the electron-donating dye precursor represented by the general formula (1) and the electron-accepting compound represented by the general formula (3) or (4) is dispersed and put into use, or in which the electron-donating dye precursor represented by the general formula (1) is encapsulated in heat-responsive microcapsules and put into use.

Conventional known methods for forming a microcapsule that can be applied in the present invention are disclosed in U.S. Pat. Nos. 3,726,804; and 3,796,669, and the like. Preferable concrete examples include an interfacial polymerization and an internal polymerization.

To be concrete, an electron-donating dye precursor, together with a microcapsule wall precursor (wall material) and other components such as a surfactant, are dissolved into an organic solvent hard to be soluble or not to be soluble in water to form an oil phase, which is added into an aqueous solution (water phase) including a water-soluble polymer and, if necessary, other components such as a surfactant, the oil phase and the water phase are emulsified with a homogenizer or the like and a temperature of the emulsion is raised to form a polymer film (wall film) serving as a microcapsule wall at interfaces between the oil phase and the water phase and to thereby form a microcapsule dispersion solution. At this time, the microcapsule wall precursor (wall material) may be incorporated not into the oil phase but into the water phase, or alternatively, into both of the oil phase and the water phase.

Examples of polymer materials (wall materials) serving as a wall film include polyurethane resin, polyurea resin, polyamide resin, polyester resin, polycarbonate resin, aminoaldehyde resin, melamine resin, polystyrene resin, styrene-acrylate copolymer resin, styrene-methacrylate copolymer resin, gelatin, polyvinyl alcohol and the like. A preferable example is microcapsules having a wall film made of polyurethane/polyurea resin.

Description will be given of an example manufacturing method of a microcapsule (polyurea/polyurethane wall) encapsulating an electron-donating precursor below.

At first, an electron-donating dye precursor is dissolved or dispersed into an hydrophobic organic solvent (if necessary, including a low boiling point solvent) serving as cores of microcapsules to thereby form an oil phase serving as the cores of microcapsules. At this time, preferably added into the oil phase are a polyvalent isocyanate as a wall material and a surfactant for the purpose to homogeneously emulsify the oil phase and stabilize the resultant emulsion. Besides, properly added into the oil phase are additive agents such as an anti-fading agent and an anti-stain agent.

In succession, thus prepared oil phase is emulsified into a water phase. At this time, an aqueous solution of a water-soluble polymer is employed as the water phase. After the oil phase is put into the water phase, both phases, combined, are emulsified with a homogenizer or the like. In order to emulsify homogeneously the both phases and to stabilize the emulsion, a surfactant is preferably added into the water phase as well. Note that the water-soluble polymer not only facilitates homogeneous dispersion, but also acts as a dispersing medium to stabilize the emulsion.

In the emulsion having an oil dispersed state in the water phase medium, a polymerization of a polyvalent isocyanate occurs at an interface between the oil phase and the water phase to form a polyurea wall.

A polyvalent isocyanate compound is preferably a compound having a tri- or higher functional isocyanate group. The polyvalent isocyanate may also be a difunctional isocyanate compound. Concrete examples thereof include: xylenediisocyanate and a compound obtained by hydrogenation thereof; hexamethylenediisocyanate; tolylenediisocyanate and a compound obtained by hydrogenation thereof; a dimer or a trimer of diisocyanate (a biuret compound or isocyanurate) such as isophoronediisocyanate, an adduct of polyol such as trimethylolpropane and a difunctional isocyanate such as xylylenediisocyanate; a compound obtained by incorporating a high molecular weight compound such as a polyether having an active hydrogen, for example a polyethylene oxide, into an adduct between a polyol such as trimethylolpropane and a difunctional isocyanate such as xylylenediisocyanate; a formalin condensate of benzeneisocyanate; and the like.

Other preferable compounds are disclosed in JP-A Nos. 62-212190, 4-26189, 5-317694, Japanese Patent Application No. 8-268721 and the like.

An amount of usage of a polyvalent isocyanate is determined so that an average particle diameter of microcapsules falls in the range of from 0.3 to 12 µm and a wall thickness falls in the range of from 0.01 to 0.3 µm. An average dispersion particle diameter is generally on the order in the range of from 0.2 to 10 µm.

The hydrophobic organic solvent that dissolves or disperses an electron-donating dye precursor therein in preparation of the oil phase described above is preferably an organic solvent of a boiling point in the range of from 100 to 300° C. Examples thereof include alkylnaphthalene, alkyldiphenylethane, alkyldiphenylmethane, alkylbiphenyl, alktlterphenyl, chlorinated paraffin, phosphate esters, maleate esters, adipate esters, phthalate esters, benzoate esters, carbonate esters, ethers, sulfate esters, sulfonate esters and the like. The compounds may be used as a mixture of two or more kinds.

In the case where a solubility of an electron-donating dye precursor into an organic solvent is low, the following low boiling point solvent with a high solubility of the electron-donating dye precursor thereinto may be additionally used as a second component: ethyl acetate, propyl acetate, isopropyl acetate, butyl acetate, methylene chloride, tetrahydrofuran, acetonitrile, acetone and the like.

That is, an electron-donating dye precursor preferably has a proper solubility in a hydrophobic organic solvent or a low boiling point solvent. To be concrete, a solubility of an electron-donating dye precursor in such an organic solvent is preferably 5% or higher in order to enable concentration adjustment of an electron-donating dye precursor to be facilitated. Note that solubility in water is preferably 1% or lower.

A water-soluble polymer used in the water phase is preferably a water-soluble polymer with a solubility in water of 5% or higher at a temperature to be emulsified. Examples thereof include polyvinyl alcohol and a modified compound therefrom; polyacrylic acid amide and a modified compound therefrom; ethylene-vinyl acetate copolymer; styrene-maleic anhydride copolymer; ethylene-maleic anhydride copolymer; isobutylene-maleic anhydride copolymer; polyvinylpyrrolidone; ethylene-acrylic acid copolymer; vinyl acetate-acrylic acid copolymer; carboxymethylcellulose; methylcellulose; casein, gelatin; starch derivative; gum arabic; sodium alginate and the like.

The water-soluble polymer preferably has no or low reactivity with an isocyanate compound. For example, a compound which has a reactive amino group in a molecular chain such as gelatin desirably neutralizes a reactivity of the amino group by modification or the like in advance.

The emulsification can be conducted with one properly selected from the group of known emulsifiers such as a homegenizer, a Manton-Gaulin, a supersonic disperser, a dissolver, kdmill and the like. After the emulsification, the emulsion is heated at a temperature in the range of from 30 to 70° C. in order to accelerate a capsule wall forming reaction. During the reaction, in order to prevent coagulation between capsules, it is required to add water to thereby lower a collision probability between capsules or to sufficiently agitate the emulsion. A dispersant for prevention of coagulation may be added into the emulsion during the reaction. Generation of a carbon dioxide gas is observed along with the progress of a polymerization reaction and the end of gas generation can be regarded roughly as an end point of the capsule wall forming reaction. Usually, by continuing the reaction for a few hours, there can be obtained microcapsules encapsulating an electron-donating dye precursor, which are a target product.

On the other hand, in preparation of a coating solution for forming a thermal recording layer (a thermal recording layer coating solution), an electron-accepting compound represented by the general formula (3) or (4) (and if necessary, together with a different electron-accepting compound) causing the electron-donating dye precursor to develop a color can also be used as solid dispersion as described above, while it is preferable that after the electron-accepting compound is dissolved, in advance, into a high boiling point organic solvent hardly soluble or insoluble in water, the solution containing the electron-accepting compound is mixed into a polymer aqueous solution (water phase) containing a surfactant and/or a water-soluble polymer as a protective colloid and the mixture is emulsified with a homogenizer or the like and the emulsion is used as the component of the coating solution. If necessary, a low boiling point solvent may be used as a dissolution auxiliary.

An electron-accepting compound represented by the general formula (3) or (4) (and if necessary, together with another electron-accepting compound) and an organic base and the like can be individually emulsified or can be mixed together and then dissolved into a high boiling point solvent, followed by emulsification. Preferable emulsion particle diameters are 1 µm or less.

The high boiling point organic solvent can be properly selected from high boiling point oils disclosed in, for example, JP-A No. 2-141279. From the viewpoint of emulsion stability, esters are preferable and tricresyl phosphate is particularly preferable. Examples of the low boiling point solvent as dissolution auxiliary described above are similar to those of the low boiling point solvent described above in an oil phase.

A surfactant contained in a water phase that is properly selected can be an anionic or nonionic surfactant causing neither precipitation nor coagulation with a water-soluble polymer. Examples thereof include sodium alkylbenzenesulfonate, sodium alkylsulfate, sulfosuccinic acid dioctyl sodium salt, polyalkylene glycol (for example, polyoxyethylenenonylphenyl ether) and the like.

The present invention may be directed to a multicolor thermal recording material comprising plural thermal recording layers on a substrate, wherein at least one layer of the thermal recording layers includes an electron-donating dye precursor and an electron-accepting compound, and at least one kind of the electron-donating dye precursor is a compound represented by the general formula (1). In this case, the electron-donating dye precursor is preferably a compound represented by the general formula (2). At least one kind of the electron-accepting compound is preferably a compound represented by the general formula (3) or the general formula (4).

In the case where plural thermal recording layers are formed on a substrate, a thermal recording material having a multicolor thermal recording layer can be obtained by altering a hue of a developed color in each of the thermal recording layers.

That is, if hues of developed colors of the thermal recording layers are selected so as to be the respective three primary colors of yellow, magenta and cyan in subtractive color mixing, a full-color image recording is enabled. In this case, as the thermal recording layer (the lowest layer) closest to the substrate, a thermal recording layer related to the present invention including an electron-donating dye precursor represented by the general formula (1) and an electron-accepting compound represented by the general formula (3) or (4) is formed. Two-or more thermal recording layers of different color hues from one another may be formed on the thermal recording layer, examples of which layers include a layer including a diazonium color developing system of a combination of a diazonium salt and a coupler that reacts with the diazonium compound while heated to develop a color, a layer including a base color developing system developing a color by contact with a basic compound, a layer including a chelate color developing system and a layer including a color developing system that reacts with a nucleophilic agent to cause an elimination reaction and develop a color.

The preferable range of a coating amount of an electron-donating dye precursor and the preferable range of a content of an electron-accepting compound in a thermal recording layer in this case is similar to the corresponding ranges described above. A mode of usage of the electron-donating dye precursor or the electron-accepting compound is preferably such that at least one of the electron-donating dye precursor and the electron-accepting compound is dispersed, or alternatively, such that the electron-donating dye precursor is encapsulated in microcapsules.

Herein, a thermal recording layer including a diazonium color developing system is preferably a photo fixing type thermal recording layer. A diazonium salt, and a coupler, which are color developing components included in the photo fixing type thermal recording layer, and a basic material accelerating a color developing reaction of the color developing components and the like can be properly selected among compounds having been conventionally known. Examples thereof are disclosed in JP-B Nos. 4-75147, 6-55546, 6-79867, JP-A Nos. 4-201483, 60-49991, 60-242094, 61-5983, 63-87125, 4-59287, 5-185717, 7-88356, 7-96671, 8-324129, 9-38389, 5-185736, 5-8544, 59-190866, 62-55190, 60-6493, 60-259492, 63-318546, 4-65291, 5-204089, 8-310133, 8-324129, 9-156229, 9-175017 and the like.

A layer structure of a full-color thermal recording material may be in a mode as described below, for example. However, it should be understood that no specific limitation is imposed thereon.

The layer structure of the full-color thermal recording material may be of such a structure in which two kinds of diazonium salts having different photo-sensitive wavelengths combined with coupler compounds which react with the respective diazonium salts when heated to develop different color hues from each other are incorporated in different layers, and the corresponding two thermal recording layers (B) and (C) having different developed color hues from each other are stacked on a thermal recording layer (A) of the present invention, which is formed on a substrate.

To be concrete, a full-color thermal recording material may have a layer structure in which a first thermal recording layer, a second thermal recording layer, and a third thermal recording layer are sequentially stacked in this order on the substrate starting with the first thermal recording layer, wherein the first thermal recording layer (A layer) related to the present invention includes an electron-donating dye precursor represented by the general formula (1) and an electron-accepting compound represented by the general formula (3) or (4), the second thermal recording layer (B layer) includes a diazonium salt having a maximum absorption wavelength of $360\pm20$ nm and a coupler compound which reacts with the diazonium salt when heated to develop a color and the third thermal recording layer (C layer) includes a diazonium salt having a maximum absorption wavelength of $400\pm20$ nm and a coupler compound which reacts with the diazonium salt when heated to develop a color.

In the case of a multicolor thermal recording layer, recording can be conducted this way:

First of all, the third thermal recording layer (C layer) is heated to cause the diazonium salt and the coupler included in the layer to develop a color. Then, the thermal recording material is irradiated with light of $400\pm20$ nm in wavelength to decompose an unreacted diazonium salt included in the C layer. Then, heat is applied to the thermal recording material sufficiently to cause the diazonium salt and the coupler included in the second thermal recording layer (B layer) to develop a color. At this time, the C layer is also strongly heated simultaneously with the B layer, whereas the diazonium salt has been decomposed to thereby lose its color developing ability and develop no additional color in the C layer. Thereafter, the thermal recording material is irradiated with light of $360\pm20$ nm in wavelength to decompose unreacted diazonium salt included in the B layer. Finally, heat is applied to the thermal recording material sufficiently to cause the thermal recording layer (A layer) related to the present invention to develop a color. At this time, the C layer and the B layer are strongly heated simultaneously, whereas the diazonium salts have been decomposed to thereby lose their color developing abilities and develop no additional color.

A multicolor thermal recording material formed by stacking plural thermal recording layers of different developed color hues from one another preferably further comprises an intermediate layer in order to prevent color mixing. The intermediate layer includes a water-soluble polymer compound. Examples thereof include polyvinyl alcohol, modified polyvinyl alcohol, methylcellulose, sodium polystyrenesulfonate, styrene-maleic acid copolymer, gelatin and the like.

A thermal recording material of the present invention, as described above, includes an electron-donating dye precursor represented by the general formula (1) and an electron-accepting compound represented by the general formula (3) or (4) as color developing components; therefore, developable colors ranging from blue to cyan, and enabling an image with a good chroma to be attained.

In a thermal recording material of the present invention, examples of substrates include paper, coated paper, laminate paper and synthetic paper or the like; films such as a polyethylenephthalate film, a triacetylcellulose film, a polyethylene film, a polystyrene film, a polycarbonate film, metal sheets made of aluminum, zinc, copper and the like and the substrates described above, surfaces of which have been treated with various kinds of treatment, such as a surface treatment, undercoating, metal vapor deposition and the like. Substrates that can be useful as reference are described in Research Disclosure, Vol. 200, December, 1980, Item 20036, Section XVII. Various layers adapted for purposes can be provided on a substrate if necessary, examples of which include an anti-halation layer on a front surface of the substrate, and a sliding layer, anantistatic layer, a curling preventive layer, a pressure-sensitive adhesive layer and the like on a rear surface of the substrate.

EXAMPLES

Below shown are examples, while it should be understood that the present invention is not limited to the examples. Note that the symbol % represents % by mass unless otherwise specified.

(Example 1)
Synthesis of Compound 5

Added into a mixed solvent composed of 10 ml of acetic acid and 20 ml acetic anhydride were 19.5 parts of N,N-di-n-propyl-N'-Benzoylaminocarbonyl-m-phenylenediamine, 22.5 parts of (1-ethyl-2-methylindole-3-yl)(3-carboxypyridine-2-yl)ketone, and the mixed solvent and the additives were stirred at 90° C. for 5 hours. The reaction solution was cooled down to room temperature and ethyl acetate was added into the solution to cause crystallization to occur, followed by filtration of the solution to separate the crystals. The raw product was dissolved into heated ethyl acetate and the solution thus obtained was cooled to obtain 12.6 parts of Compound 5 shown as a concrete example in white crystalline state.

Shown below are structural data from $^1$H-NMR spectrum of Compound 5:

$^1$H-NMR(CDCl$_3$)δ(TMS, ppm) 0.95 (6H, t), 1.21 (3H, t), 1.61 (4H, m), 2.01 (3H, s), 3.24 (4H, t), 3.82 (2H, t), 6.42 (1H, dd), 6.61 (2H, m), 6.78 (1H, t) 6.90 (1H, d), 7.03 (1H, dd), 7.28 (4H, m), 7.51 (4H, m), 8.20 (1H, dd), 8.28 (1H, s), 8.96 (1H, dd)

(Example 2)
Synthesis of Compound 8

Compound 8 as the concrete example was obtained in a similar manner to the case of Example 1 except for usage of an m-phenylenediamine compound and a pyridinecarboxylic acid, both corresponding to Compound 8.

Shown below are structural data from $^1$H-NMR spectrum of Compound 8:

$^1$H-NMR(CDCl)$_b$(TMS, ppm) 0.96 (6H, t), 1.08 (3H, t), 1.21 (3H, t), 2.11 (3H, s), 3.20 (4H, t), 3.81 (2H, m), 3.96 (2H, t), 6.08 (1H, s), 6.40 (1H, dd), 6.51 (1H, d), 6.80 (2H, m), 6.98 (1H, s) 7.18 (1H, d), 7.20 (1H, s), 7.43 (1H, m), 8.23 (1H, dd), 8.92 (1H, dd), 8.95 (1H, S)

(Example 3)
Preparation of Thermal Recording Material (1)
Preparation of Phthalated Gelatin Solution The following components were mixed together: 32 parts of phthalated gelatin (manufactured by Nitta Gelatin Inc. with a trade name of #801 Gelatin), 0.9143 part of 1,2-benzothiazoline-3-on (as a 3.5% solution in methanol manufactured by Daito Chemical Industries, Ltd.) and 367.1 parts of ion exchanged water, and the mixture was dissolved at 40° C. to obtain a phthalated gelatin aqueous solution.
Preparation of Thermal Recording Layer Coating Solution
Preparation of Electron-Donating Dye Precursor Dispersion Solution a

Mixed into 5.63 parts of the phthalated gelatin solution obtained in the above preparation were 12.08 parts of ion exchanged water, 1.50 parts of Compound 5 as a concrete example and 0.38 part of a 2% aqueous solution of sodium 2-ethylhexylsuccinate, and the mixture was dispersed all night long with a ball mill to obtain an electron-donating dye precursor dispersion solution a. An average particle diameter of the electron-donating dye precursor in a dispersed state in the dispersion solution was measured to be 1.2 μm with a particle diameter distribution measuring instrument LA-910 (manufactured by Horiba, Ltd.).
Preparation of Salicylic Acid Derivative Metal Salt Dispersion Solution Mixed into 3.75 parts of the phthalated gelatin solution obtained in the above preparation were 10.02 parts of ion exchanged water, 5.0 parts of the salicylic acid derivative metal salt already exemplified (exemplified Compound 85) and 1.25 parts of a 2% aqueous solution of sodium 2-ethylhexylsuccinate, and the mixture was dispersed all night long with a ball mill to obtain a salicylic acid derivative metal salt dispersion solution. An average particle diameter of the salicylic acid derivative metal salt in a dispersed state in the dispersion solution was measured to be 0.5 μm with a particle diameter distribution measuring instrument LA-910 (manufactured by Horiba, Ltd.) and a solid matter concentration was obtained to be 26.3%.
Preparation of Thermal Recording Layer Coating Solution a The electron-donating dye precursor dispersion solution a and the salicylic acid derivative metal salt dispersion solution in the above preparations were mixed together so that a ratio (in mass) of electron-donating dye precursor/salicylic acid derivative metal salt was 1/20 to obtain a thermal recording layer coating solution a.
Preparation of Intermediate Layer Coating Solution
Preparation of Alkali-Treated Gelatin Aqueous Solution (1)

The following components were mixed together: 100.0 parts of an alkali-treated low ion gelatin (manufactured by Nitta Gelatin Inc. with a trade name of #750 Gelatin), 2.857 parts of 1,2-benzothiazoline-3-on (as a 3.5% solution in methanol manufactured by Daito Chemical Industries, Ltd.), 0.5 part of calcium hydroxide and 521.643 parts of ion exchanged water, and the mixture was dissolved at 50° C. to obtain an alkali-treated gelatin aqueous solution (1) for use in preparation of an intermediate layer coating solution.
Preparation of Intermediate Layer Coating Solution The following components were mixed together: 10.0 parts of the alkali-treated gelatin aqueous solution (1) obtained in the above preparation, 0.05 part of sodium (4-nonylphenoxytrioxyethylene)butylsulfonate (as a 2.0% aqueous solution manufactured by Sankyo Chemical Industries, Ltd.), 1.5 parts of boric acid (as a 4% aqueous solution), 0.19 part of a 5% aqueous solution of polystyrenesulfonic acid (partially potassium hydroxide neutralized type), 3.42 parts of a 4% aqueous solution of the following compound (J), 1.13 part of a 4% aqueous solution of the following compound (J') and 0.67 part of ion exchanged water, to thereby obtain an intermediate layer coating solution.

Compound (J)

Compound (J')

Preparation of Protective Layer PVA Solution

The following components were mixed together: 160 parts of vinyl alcohol/alkylvinyl ether copolymer (manufactured by Denki Kagaku Kogyo Kabushiki Kaisha with a trade name of EP-130), 8.74 parts of a mixture of sodium alkylsulfonate and polyoxyethylenealkyl ether phosphate ester (as a 54% aqueous solution manufactured by Toho Chemical Industry Co., Ltd. with a trade name of Neoscore CM-57) and 3832 parts of ion exchanged water, and the mixture was dissolved at 90° C. for 1 hour to obtain a homogeneous protective layer PVA solution.

Preparation of Thermal Recording Material

A polyethylene terephthalate (PET) substrate with a thickness of 75 μm was prepared as a substrate and the thermal recording layer coating solution a obtained in the above preparation was applied on the PET substrate with a mayor bar so that a coating amount of an electron-donating dye precursor was 0.361 g/cm² and the wet coat was dried to form a thermal recording layer. In succession, the intermediate layer coating solution obtained in the above preparation was applied; and dried thereon so that a solid matter coating amount was 2.39 g/cm² and the protective layer PVA solution obtained in the above preparation was further applied and dried thereon so that a solid matter amount was 1.39 g/cm$^a$ to obtain a thermal recording material (1) of Example 3.

(Example 4)

A thermal recording material (2) of Example 4 was obtained in a similar manner to the case of Example 3 with the exception that the electron-donating dye precursor used in the preparation of the electron-donating dye precursor dispersion solution a in Example 3 was replaced with Compound 8 as the concrete example.

(Comparative Example 1)

A thermal recording material (3) of Comparative Example 1 was obtained in a similar manner to the case of Example 3 with the exception that the electron-donating dye precursor used in the preparation of the electron-donating dye precursor dispersion solution a in Example 3 was replaced with Compound 110 as the concrete example.

(Comparative Example 2)

A thermal recording material (4) of Comparative Example 2 was obtained in a similar manner to the case of Example 3 with the exception that the electron-donating dye precursor used in the preparation of the electron-donating dye precursor dispersion solution a in Example 3 was replaced with the following compound 111:

TABLE 10

[Chemical structure shown]

| Compound | R⁶ | Y |
|---|---|---|
| 110 | c-Hex | O |
| 111 | Ph | O |

TABLE 10-continued

[Chemical structure shown]

| Compound | R⁶ | Y |
|---|---|---|
| 112 | ⁿBu | O |
| 113 | Ph | S |

Evaluation of Physical Properties in Solution

Figure 1:
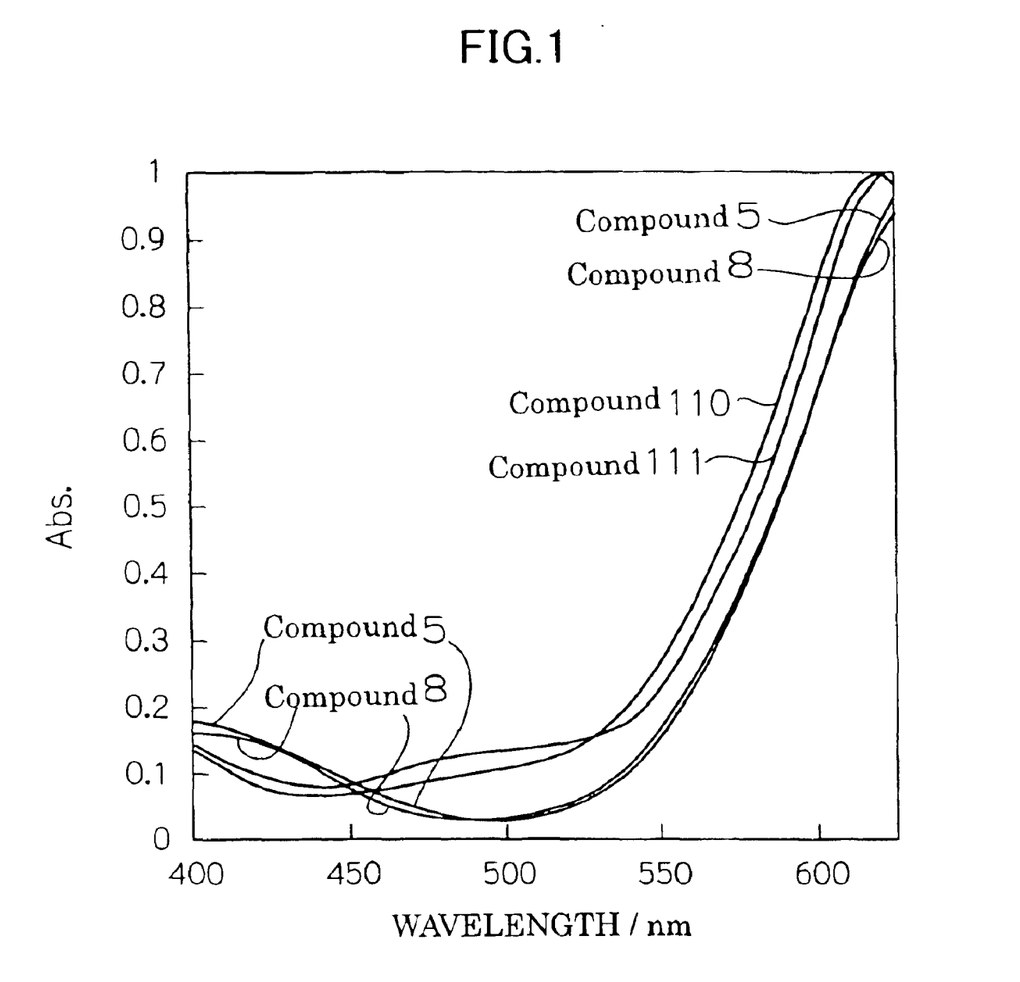
FIG. 1 is a graph showing transmission spectra of compounds 5, 8, 110 and 111.

Comparison between the electron-donating dye precursors used in Examples 3 and 4 (Compounds 5 and 8) and the electron-donating dye precursors (Compounds 110 and 111) used in Comparative Examples 1 and 2 in a solution was conducted. Transmission spectra of solutions obtained by respectively adding the electron-donating dye precursors into toluene so as to be 0.02 mol/l in concentration and further adding zinc salicylate into the toluene solutions so as to be 0.08 mol/l in concentration were measured with a spectrometer MPS 2000 type (manufactured by Shimadzu Corporation). Results of the measurement are shown in FIG. 1.

Then, an absorbance (Abs.) at a maximum absorption th of each compound was standardized as 1 and an absorbance at 500 nm was obtained under the standardization. Results of this measurement are shown in Table 11. Measurement was further conducted with respect to absorbance values at 500 nm for cases in which Compounds 112 and 113 were used as an electron-donating dye precursor according to a method similar to that described above. Results of this measurement are also shown in Table 11.

TABLE 11

| | Compound 5 | Compound 8 | Compound 110 | Compound 111 | Compound 112 | Compound 113 |
|---|---|---|---|---|---|---|
| Abs. (500 nm) | 0.029 | 0.027 | 0.110 | 0.135 | 0.120 | 0.124 |

Image Formation and Evaluation

Thermal recording was conducted using a thermal head (manufactured by Kyocera Corporation with a trade name of KST) on the thermal recording materials (1) and (2) of Examples 3 and 4, and the thermal recording materials (3) and (4) of Comparative Examples 1 and 2 to obtain images in cyan on the respective materials. A reflection spectrum of a formed image was measured with a spectrometer UV 3100S type (manufactured by Shimadzu Corporation). An absorbance value at a maximum reflection wavelength was normalized as 1 in a manner similar to the case of evaluation of the above solutions and comparison was conducted between absorbance values at 500 nm.

TABLE 12

|  | Example 3 (Compound 5) | Example 4 (Compound 8) | Comparative Example 1 (Compound 110) | Comparative Example 2 (Compound 111) |
| --- | --- | --- | --- | --- |
| Abs. (500 nm) | 0.156 | 0.151 | 0.273 | 0.296 |

As is clear from Tables 11 and 12, it is found that in the case where an indolylphthalide compound of the present invention represented by the general formula (1) is used, absorbance values at 500 nm are lower in the examples than in the comparative examples, in both a solution color developed state and in a thermal recording material, and chroma levels of a cyan hue are improved in the examples as compared with the levels in the comparative examples.

According to the present invention, a thermal recording material can be obtained that forms an image in a color in the range of blue to cyan with high in chroma.

What is claimed is:

1. An indolylphthalide compound represented by general formula (1):

General formula (1)

wherein $R^1$ and $R^2$ each independently represent a hydrogen atom, an alkyl group, a cycloalkyl group, an aralkyl group or an aryl group, provided that $R^1$ and $R^2$ do not represent a hydrogen atom at the same time, and $R^1$ and $R^2$ may form a bond therebetween to collectively represent a single cycloamino structure; $R^3$ represents an alkyl group, a cycloalkyl group, an aralkyl group, an aryl group or an alkoxy group; $R^4$ and $R^5$ each independently represent a hydrogen atom, an alkyl group or an aryl group; $X^1$, $X^2$, $X^3$ and $X^4$ each independently represent N or CH; and Y represents an oxygen atom or a sulfur atom.

2. An indolylphthalide compound according to claim 1, wherein, in general formula (1), $X^2$, $X^3$, and $X^4$ each represent CH, and Y represents an oxygen atom.

3. A thermal recording material comprising, on a substrate, a thermal recording layer which includes an electron-donating dye precursor and an electron-accepting compound, wherein at least one kind of the electron-donating dye precursor is represented by general formula (1):

General formula (1)

wherein $R^1$ and $R^2$ each independently represent a hydrogen atom, an alkyl group, a cycloalkyl group, an aralkyl group or an aryl group, provided that $R^1$ and $R^2$ do not represent a hydrogen atom at the same time, and $R^1$ and $R^2$ may form a bond therebetween to collectively represent a single cycloamino structure; $R^3$ represents an alkyl group, a cycloalkyl group, an aralkyl group, an aryl group or an alkoxy group; $R^4$ and $R^5$ each independently represent a hydrogen atom, an alkyl group or an aryl group; $X^1$, $X^2$, $X^3$ and $X^4$ each independently represent N or CH; and Y represents an oxygen atom or a sulfur atom.

4. A thermal recording material according to claim 3, wherein, in general formula (1), $X^2$, $X^3$, and $X^4$ each represent CH, and Y represents an oxygen atom.

5. A thermal recording material according to claim 3, wherein at least one kind of the electron-accepting compound is represented by general formula (3):

General formula (3)

wherein $Z^1$, $Z^2$, $Z^3$ and $Z^4$ each independently represent a hydrogen atom, an alkyl group, a cycloalkyl group, an aralkyl group, an aryl group, a hydroxyl group or a halogen atom; n represents 2 or 3; and M represents Al, Zn or Cu.

6. A thermal recording material according to claim 3, wherein at least one kind of the electron-accepting compound is represented by general formula (4):

General formula (4)

wherein $A^1$ and $A^2$ each independently represent an alkyl group, a cycloalkyl group, an aralkyl group, an aryl group, a hydroxyl group or a halogen atom; n and m each independently represent a number from 0 to 4, and, in the case where n and m both are 2 or more, $A^1$ and $A^2$ may be the same as or different from each other; and L represents a single bond or a divalent linkage group.

7. A thermal recording material according to claim 3, wherein at least one of the electron-donating dye precursor and the electron-accepting compound is dispersed.

8. A thermal recording material according to claim 3, wherein the electron-donating dye precursor is encapsulated in microcapsules.

9. A thermal recording material according to claim 3, wherein a coating amount of the electron-donating dye precursor is in a range of 0.1 to 2.0 g/m².

10. A multicolor thermal recording material comprising plural thermal recording layers on a substrate, wherein at least one layer of the thermal recording layers includes an electron-donating dye precursor and an electron-accepting compound, and at least one kind of the electron-donating dye precursor is represented by general formula (1):

General formula (1)

wherein $R^1$ and $R^2$ each independently represent a hydrogen atom, an alkyl group, a cycloalkyl group, an aralkyl group or an aryl group, provided that $R^1$ and $R^2$ do not represent a hydrogen atom at the same time, and $R^1$ and $R^2$ may form a bond therebetween to collectively represent a single cycloamino structure; $R^3$ represents analkyl group, a cycloalkyl group, an aralkyl group, an aryl group or an alkoxy group; $R^4$ and $R^5$ each independently represent a hydrogen atom, an alkyl group or an aryl group; $X^1$, $X^2$, $X^3$ and $X^4$ each independently represent N or CH; and Y represents an oxygen atom or a sulfur atom.

11. A multicolor thermal recording material according to claim 10, wherein, in general formula (1), $X^2$, $X^3$, and $X^4$ each represent CH, and Y represents an oxygen atom.

12. A multicolor thermal recording material according to claim 10, wherein at least one kind of the electron-accepting compound is represented by general formula (3):

General formula (3)

wherein $Z^1$, $Z^2$, $Z^3$ and $Z^4$ each independently represent a hydrogen atom, an alkyl group, a cycloalkyl group, an aralkyl group, an aryl group, a hydroxyl group or a halogen atom; n represents 2 or 3; and M represents Al, Zn or Cu.

13. A multicolor thermal recording material according to claim 10, wherein at least one kind of the electron-accepting compound is represented by general formula (4):

General formula (4)

wherein $A^1$ and $A^2$ each independently represent an alkyl group, a cycloalkyl group, an aralkyl group, an aryl group, a hydroxyl group or a halogen atom; n and m each independently represent a number from 0 to 4, and, in the case where n and m both are 2 or more, $A^1$ and $A^2$ may be the same as or different from each other; and L represents a single bond or a divalent linkage group.

14. A multicolor thermal recording material according to claim 10, wherein at least one of the electron-donating dye precursor and the electron-accepting compound is dispersed.

15. A multicolor thermal recording material according to claim 10 wherein the electron-donating dye precursor is encapsulated in microcapsules.

16. A multicolor thermal recording material according to claim 10, wherein a coating amount of the electron-donating dye precursor is in a range of 0.1 to 2.0 g/m².

17. A multicolor thermal recording material according to claim 10, having a layer structure in which a first thermal recording layer, a second thermal recording layer, and a third thermal recording layer are sequentially stacked in this order on the substrate starting with the first thermal recording layer, wherein:

the first thermal recording layer includes an electron-donating dye precursor represented by general formula (1) and an electron-accepting compound represented by general formula (3) or (4);

the second thermal recording layer includes a diazonium salt having a maximum absorption wavelength of 360±20 nm and a coupler compound which reacts with the diazonium salt when heated to develop a color; and the third thermal recording layer includes a diazonium salt having a maximum absorption wavelength of 400±20 nm and a coupler compound which reacts with the diazonium salt when heated to develop a color,

General formula (1)

wherein, in general formula (1) $R^1$ and $R^2$ each independently represent a hydrogen atom, an alkyl group, a cycloalkyl group, an aralkyl group or an aryl group, provided that $R^1$ and $R^2$ do not represent a hydrogen atom at the same time, and $R^1$ and $R^2$ may form a bond therebetween to collectively represent a single cycloamino structure; $R^3$ represents an alkyl group, a cycloalkyl group, an aralkyl group, an aryl group or an alkoxy group; R and $R^5$ each independently represent a hydrogen atom, an alkyl group or an aryl group; $X^1$, $X^2$, $X^3$ and X each independently represent N or CH; and Y represents an oxygen atom or a sulfur atom, General formula (3)

wherein, in general formula (3), $Z^1$, $Z^2$, $Z^3$ and $Z^4$ each independently represent a hydrogen atom, an alkyl group, a cycloalkyl group, an aralkyl group, an aryl group, a hydroxyl group or a halogen atom; n represents 2 or 3; and M represents Al, Zn or Cu, General formula (4)

wherein, in general formula (4), $A^1$ and $A^2$ each independently represent an alkyl group, a cycloalkyl group, an aralkyl group, an aryl group, a hydroxyl group or a halogen atom; n and m each independently represent a number from 0 to 4, and, in the case where n and m both are 2 or more, $A^1$ and $A^2$ may be the same as or different from each other; and L represents a single bond or a divalent linkage group.

18. A multicolor thermal recording material according to claim 17, further comprising an intermediate layer.

* * * * *